United States Patent [19]

Cobb

[11] 3,962,134
[45] June 8, 1976

[54] MAGNESIUM-ALUMINUM-SILICATE-PHOSPHATE CATALYSIS FOR AMMONIALYTIC CLEAVAGE OF LACTAMS TO FORM OMEGA-AMINONITRILES

[75] Inventor: Raymond L. Cobb, Bartlesville, Okla.

[73] Assignee: Phillips Petroleum Company, Bartlesville, Okla.

[22] Filed: Jan. 27, 1975

[21] Appl. No.: 544,647

Related U.S. Application Data

[60] Division of Ser. No. 420,879, Dec. 3, 1973, Pat. No. 3,886,196, which is a continuation-in-part of Ser. No. 329,557, Feb. 7, 1973, abandoned, which is a continuation of Ser. No. 879,635, Nov. 24, 1969, abandoned.

[52] U.S. Cl. .............................................. 252/437
[51] Int. Cl.² ......................................... B01J 27/14
[58] Field of Search .................. 252/437; 260/465.2

[56] References Cited
UNITED STATES PATENTS
3,579,558   5/1971   Immel et al. .................... 260/465.2

*Primary Examiner*—J. Poer

[57] ABSTRACT

Ammonialytic cleavage of lactams to ω-aminonitriles is effectively promoted by the use of compositions of magnesium-aluminum-silicate-phosphate on a substrate as catalysts.

12 Claims, No Drawings

MAGNESIUM-ALUMINUM-SILICATE-PHOSPHATE CATALYSIS FOR AMMONIALYTIC CLEAVAGE OF LACTAMS TO FORM OMEGA-AMINONITRILES

This application is a divisional application of Ser. No. 420,879 filed Dec. 3, 1973, now U.S. Pat. No. 3,886,196, issued May 27, 1975; which was a continuation-in-part of Ser. No. 329,557 filed Feb. 7, 1973, now abandoned; which was a continuation of Ser. No. 879,635 filed Nov. 24, 1969, now abandoned.

BACKGROUND OF THE INVENTION

This invention relates to the production of $\omega$-aminonitriles from the corresponding lactams. In another aspect, it relates to unique magnesium-aluminum-silicate-phosphate catalysts.

Lactams are internal or cyclic amides. The reaction involved with the catalysts of my invention converts the lactam to an $\omega$-aminonitrile by a cleavage reaction with ammonia. The reaction involves removal of the oxygen from the lactam molecule with the formation of water, and the addition of another nitrogen to the molecule to form a nitrile group on one end of a chain-like molecule with an amino group on the other end. There can be various substituents around the lactam ring, and consequently along the $\omega$-aminonitrile chain.

The aminonitriles are valuable chemicals since they are readily convertible to diamines or to other compounds useful as polymer precursors. For example, commercially available nylons are essentially long linear chains of amide

groups separated by 4 to 11 methylene

groups. One basic method of preparation of such nylons utilizes a condensation reaction of diamines with dibasic acids, for example hexamethylenediamine with adipic acid.

It is desirable to obtain maximum conversion of the lactam to the corresponding $\omega$-aminonitrile in order to have a commerciably feasible production process.

OBJECTS OF THE INVENTION

It is an object of my invention to provide catalysts effective to improve the ammonialytic cleavage of lactams to the corresponding $\omega$-aminonitriles. Another object is to provide for maximum effectiveness in one or more of yield and conversion in the production of $\omega$-aminonitriles from lactams.

Other aspects, objects, and the several advantages of my invention will be apparent to one skilled in the art to which the invention most nearly pertains from the following description and from my appended claims.

BRIEF SUMMARY OF THE INVENTION

I have discovered that catalysts of magnesium-aluminum-silicate-phosphate composition serve to greatly enhance this conversion reaction to which I refer. These catalysts are unique, and are peculiarly effective in the conversion of lactams to $\omega$-aminonitriles by improving at least one of conversion and yield for the ammonialytic cleavage under quite moderate reaction conditions.

DESCRIPTION OF THE INVENTION

The ammonialytic cleavage reaction to which I have referred can be illustrated by the following:

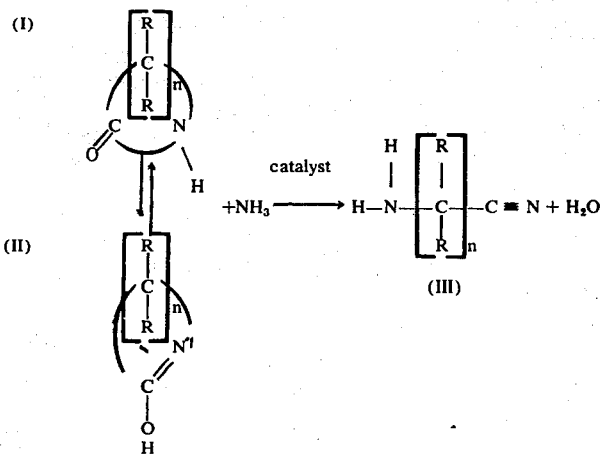

The lactam as shown by formula (I) above is called a lactim in the tautomeric or enol form as shown by formula (II) above. The reaction, perhaps, may be more readily visualized as being between the enol form and the ammonia. Whether the cleavage is considered as occurring on one side or the other of the nitrogen of the lactam is immaterial. The resulting non-cyclic $\omega$-aminonitrile is respresented by formula (III) above.

Various substituents can be on the carbons of the lactam ring and consequently along the carbon chain of the $\omega$-aminonitrile, as shown by the R symbols in formulas given above. R can be hydrogen, alkyl, cycloalkyl, aryl, or combinations thereof such as alkylaryl or arylalkyl and the like, and can have in the range of 1 to about 8 carbon atoms provided that not more than 10 carbon atoms are contained in the total of R groups per lactam molecule. The $n$ is an integer, and can range from about 3 to 9, inclusive.

EXAMPLES

The examples which follow demonstrate the operability and effectiveness of the catalysts as I apply them to the ammonialytic cleavage reaction according to the process of my invention. These examples should be considered illustrative and not as limiting. The examples represent a series of runs with varying catalysts and with varying reaction temperatures. The evaluation of the results of these runs was made with the aid of analysis by gas-liquid chromatography. With this procedure, the chromatographic peaks corresponding to reactants and products were identified and compared with one another on the basis of area per cent, the area for each effluent constituent being defined by the base line of the chromatographic curve and the chromatographic peak for that constituent. While area per cent is not necessarily identical with either weight per cent or mole per cent, it is nevertheless, a commonly used and reliable method for comparing the relative effects of reaction variables, such as different catalysts, within a given reaction system.

In the examples given, conversion is determined by subtracting the area per cent of lactam in the catalyst-containing reactor effluent based on the total area of the effluent excluding ammonia, from 100. Yield per cent is determined by calculating the area per cent of lactam which had been converted to the desired $\omega$-aminonitrile in the effluent from the reactor.

During each run, the stream from the catalyst-containing reactor was periodically subjected to gas liquid chromatography. The lack of a peak for the original lactam indicated complete conversion. The gas liquid chromatography peak for $\omega$-aminonitrile determined the area per cent of $\omega$-aminonitrile in the stream portion made up of the $\omega$-aminonitrile plus any unsaturated nitrile.

A series of products is formed in the ammonialytic cleavage of a lactam. These include the desired $\omega$-aminonitrile, as well as a series of minor amounts of intermediates of an unsaturated type represented by

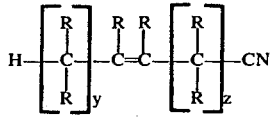

wherein $y$ and $z$ are integers such that $y + z + 2 = n$, as well as unconverted lactam, ammonia, diluent if any is used, and sometimes minor amounts of polymer. No polymer was formed, however, in any runs in the following examples.

EXAMPLE I

My catalysts for those runs of this example employing my invention were prepared using three different substrates.

The first solution was prepared using 24.7 g (gram) (0.1 mole) of magnesium sulfate heptahydrate and 66.7 g (0.1 mole) of aluminum sulfate hydrated (18H$_2$O) in 600 ml (milliliters) of total solution, using deionized water. To this first aqueous solution was then added 100 g of the particular substrate in a finely divided particulate form. The substrate was maintained in suspension in the first solution by stirring.

A second aqueous solution was prepared of 28.5 g of sodium silicate (water glass) and 30.6 g (0.1 mole) of trisodium orthophosphate hydrated (12H$_2$O) in 150 ml total solution, again using deionized water.

The second aqueous solution then was added to the first aqueous solution containing the substrate, and the whole mixture stirred for a few minutes. Thereupon, the resulting suspended material was filtered, and washed with deionized water. The filtered washed material was dried in air at 150° C. to a constant weight.

These compositions were utilized to catalyze the ammonialytic cleavage of lactam to $\omega$-aminonitrile. Compartive runs using other material under the same reaction conditions showed far inferior results, this comparatively demonstrating the high order effectiveness of the catalysts of my invention when used in this process.

For each run, caprolactam, normally a solid material, was heated to a temperature of about 130° C., and so converted to a molten or liquid state. The lactam was maintained at this temperature in a molten condition while ammonia gas was passed through the molten material at the rate of 1.9 g per minute. The ammonia gas was at one atmosphere of pressure and had been preheated to about 375° C. prior to contacting the molten lactam.

The vaporous effluent from this procedure was a mixture of ammonia and caprolactam vapor, and contained in the range of from about 75 to 100 moles of ammonia per mole of lactam. This vapor stream was then conducted to a stainless steel reactor 1 inch diameter containing about 100 cc (cubic centimeters) of catalyst. The catalyst charge was retained in the vertical tube reactor by a plug of glass wool and some alpha alumina at the bottom of the reactor.

The temperature of the reactor was controlled and varied by an electric furnace in which the reactor was contained. Thus, for each catalyst tested, the stream of ammonia and lactam vapor mixture was passed through the catalytic reactor for about 20–30 minutes, the reaction temperature was noted, and the reactor effluent was sampled for analysis by gas-liquid chromatography. This process was repeated for several reaction temperatures, samples being taken at about 275°, 300°, 330°, 360°, 400°, and 425° C. The conversion and selectivity results obtained with each catalyst in such a temperature series were plotted on a graph as a function of reaction temperature. To compare the effectiveness of the catalysts, the conversion and selectivity were read from each curve at a point corresponding to 375° C. reaction temperature. These standardized and directly comparable data so obtained from these series of reactions are shown in Table I below.

TABLE I

| Run No. | Catalyst | Conversion Area Percent | Yield Area Percent |
|---|---|---|---|
|  | Invention: |  |  |
| 1 | Magnesium-aluminum-phosphate-silicate on alumina$^{(a)}$ support | 97 | 88 |
| 2 | Magnesium-aluminum-phosphate-silicate on silica gel$^{(b)}$ support | 90 | 96 |
| 3 | Magnesium-aluminum-phosphate-silicate on diatomaceous earth$^{(c)(1)}$ support | 83 | 98 |
|  | Control Runs: |  |  |
| 4 | $\gamma$-alumina$^{(d)}$ | 90 | 25 |
| 5 | $\alpha$-alumina$^{(e)}$ | 10 | 100 |
| 6 | AlPO$_4$$^{(f)}$ | 65 | 87 |
| 7 | Mg$_3$(PO$_4$)$_2$.5H$_2$O$^{(g)}$ | 47 | 98 |

TABLE I-continued

| Run No. | Catalyst | Conversion Area Percent | Yield Area Percent |
|---|---|---|---|
| 8 | 13X molecular sieve[h] | 57 | 82 |

[a] An 80–200 mesh chromatographic grade α-alumina
[b] A 28–200 mesh silica gel (Grade 12, Fisher Co.)
[c] Laboratory grade diatomaceous earth (Johns Manville Co.)
[d] From Harshaw Chemical Co., Cleveland, Ohio, a tableted activated alumina containing 99% $Al_2O_3$, balance moisture.
[e] α-Alumina was obtained from Harshaw Chemical Co., Cleveland, Ohio. The material used was a tableted, sintered, β-alumina containing 99 percent $Al_2O_3$, remainder moisture.
[f] Laboratory grade in pellet form
[g] Laboratory grade in pellet form
[h] Commercial designation of the pore-size of a commercially available molecular sieve obtained from the Linde Division of Union Carbide Corp. For description of molecular sieves, refer to the article by D. W. Breck in 41 Journal of Chemical Education 678 and following, December, 1964. 13X indicates a pore size of about 10A.
[i] $NH_3$ flow only about 1g/min. in this run.

The data in Table I above demonstrate clearly that my magnesium-aluminum-phosphate-silicate catalysts are superior to related materials or components alone. Distinct improvement in conversion or in yield, or in both factors, is shown by the use of my catalysts.

Catalyst Preparation

My catalysts can be prepared by any suitable procedure effective to prepare the catalyst compositions I have described. Preferably, I use the method described in Example I above. A first aqueous solution is prepared from magnesium sulfate and aluminum sulfate. To this first aqueous solution is added a substrate such as alumina or silica or a combination thereof. The substrate, of course, is relatively insoluble and so makes an admixture or slurry in the first aqueous solution.

A second aqueous solution is then prepared from a silicate and an alkali metal phosphate. The second aqueous solution is then added to the first aqueous solution with the substrate, and the whole then stirred. The solid components of the mixture are then allowed to settle.

The material which separates from the admixture is my catalyst, a magnesium-aluminum-silicate-phosphate material precipitated onto the substrate. This catalyst material is then filtered or otherwise removed from the remaining solution, such as by decanting or centrifuging, washed with water, dried, to give the catalytic compositions which I employ.

Quantities of magnesium, aluminum, silicate, and phosphate compounds employed should be such that a balance of cations and anions is effected in the magnesium-aluminum-silicate-phosphate precipitated. In general, in the magnesium-aluminum-silicate-phosphate precipitated, the mole ratio of magnesium:aluminum ions can be in the range of 99:1 to 1:99, but is preferably in the range of 5:1 to 1:5; the mole ratio of silicate:phosphate ions can also be in the range of 99:1 to 1:99, but is preferably in the range of 5:1 to 1:5. The catalytic composition of substrate plus magnesium-aluminum-silicate-phosphate can contain in the range of from 0.5 to 99.5 weight per cent of magnesium-aluminum-silicate-phosphate, more preferably in the range of 15 to 50 weight per cent of magnesium-aluminum-silicate-phosphate, the remainder being the substrate to total 100 weight per cent.

In the preferred method of preparation that I have described, the term magnesium sulfates includes the natural or synthetic $MgSO_4$, anhydrous, or the monohydrate kieserite, or the heptahydrate epsomite. Various alkali metal double salts are also suitable. These latter include langbelinite $K_2SO_4·2MgSO_4$; leonite $K_2SO_4·MgSO_4·4H_2O$; $K_2SO_4·MgSO_4·6H_2O$; bloedite $Na_2SO_4·MgSO_4·4H_2O$; and ammonium double salts such as boussingaulite $(NH_4)_2SO_4·MgSO_4·6H_2O$; and the like.

The aluminum sulfate component can be obtained in various natural or synthetic forms such as the anhydrous $Al_2(SO_4)_3$; the highly hydrated alunogenite $Al_2(SO_4)_3·18H_2O$; as well as a variety of combined salts with members of the alkali metal group and including ammonium. Examples of such combined salts include kalinite $KAl(SO_4)_2·12H_2O$; $NaAl(SO_4)_2·12H_2O$; $NH_4Al(SO_4)_2$; $LiAl(SO_4)_2$; $RbAl(SO_4)_2$; $CsAl(SO_4)_2$; and the like.

For my substrates, I can use any of the naturally-occurring or synthetically prepared silicas; or any of the aluminas such as α-alumina, η-alumina, γ-alumina, and including the fluoride compound-treated aluminas; or combinations thereof such as silica-alumina, alumina-boria, alumina-zirconia, and alumina-beryllia. The term silica includes finely divided particulate sand, quartz, flint, charcedony, opal, agate, diatomite or diatomaceous earth, synthetically prepared silicon dioxide, as well as combined forms containing silica such as silica-zirconia, silica-boria, and the like. Various other substrate combinations are effective including silica-alumina-zirconia, silica-alumina-beryllia, silica-alumina-titania, silica-alumina-boria, and the like. Suitable combination substrates further include physical mixtures of two or more substrates. Any similar substrate is effective as a support.

In the preferred method of preparing my catalyst, the second aqueous solution is made up of a water-soluble silicate together with an alkali metal phosphate or ammonium phosphate. These water-soluble silicates include any of the ammonium silicates or the alkali metal silicates, disilicates, metasilicates, orthosilicates, anhydrous or hydrated. Ammonium is included, since in an aqueous solution ammonium ion closely resemble potassium ion, being virtually identical in size thereto. Only the Group IA silicates of lithium, sodium, potassium, rubidium, and cesium, and the ammonium silicates are sufficiently water-soluble to be useful. This is Group IA of the periodic table of the elements as it appears on page B-3 of the *Handbook of Chemistry and Physics*, 49th edition, Chemical Rubber Company, 1968. The soluble silicates can include the sodium silicates such as water glass $Na_2O·XSiO_2$ where X can range from about 3 to 5; sodium disilicate $Na_2Si_2O_5$; sodium metasilicate $Na_2SiO_3$; sodium orthosilicate $Na_4SiO_4$; in any of their anhydrous as well as various hydrated forms. For example, the metasilicate can be anhydrous, pentahydrated, monohydrated.

My second aqueous solution further contains an ammonium or an alkali metal phosphate, with the alkali metals being as defined above. A wide range of phosphates are suitable and effective. For example, sodium hypophosphate $Na_4P_2O_6·10H_2O$; sodium dihydrogen hypophosphate $Na_4H_2P_2O_6·6H_2O$; sodium hexametaphosphate $(NaPO_3)_6$; sodium trimetaphosphate $(NaPO_3)_3·6H_2O$; sodium orthophosphate $Na_3PO_4·12H_2O$; sodium dihydrogen orthophosphate $NaH_2PO_4$, including anhydrous, dihydrate, heptahydrate, dodecahydrate; sodium pyrophosphate monohydrate, dihydrate, and anhydrous; sodium monohydrogen orthophosphate $Na_2HPO_4$, including anhydrous, dihydrate, heptahydrate, dodecahydrate; sodium pyrophosphate $Na_4P$-

$_2O_7 \cdot 10H_2O$; sodium dihydrogen pyrophosphate $Na_2H_2P_2O_7 \cdot 6H_2O$; sodium triphosphate $Na_5P_3O_{10}$, which is frequently termed sodium tripolyphosphate; and any of the equivalent ammonium or other alkali metal phosphates; and their anhydrous, partially hydrated, or fully hydrated forms. Additionally suitable are combination salts such as microcosmic salt $NH_4NaHPO_4 \cdot 4H_2O$.

Either crystalline or powdered salts can be utilized in making up the solutions, though powdered materials usually are preferable as more quickly providing solution or dispersion. The water to make up the solutions as well as the solutions themselves can be at any convenient temperature such as room temperature, but somewhat elevated temperatures can be used, if desired, in order to more quickly provide solution or dispersion.

Other methods of preparation of my catalyst compositions are suitable. For example, it is feasible to add the substrate to my second aqueous solution, and then pour this admixture into the first aqueous solution as I have described. Or, other magnesium salts could well be used, and solutions could be made up of, for example, an alkali metal sulfate and a magnesium phosphate, since a variety of synthetic and naturally-occurring magnesium phosphate salts are slightly, though sufficiently, soluble in water, such as newberyite $MgHPO_4 \cdot H_2O$, and the like.

Nor is it necessary to make up merely two solutions. Different salts can be made up in separate solutions, and then all poured together along with addition of the substrate in order to prepare my catalysts. For example, aluminum sulfate can be dissolved separately, sodium silicate separately, magnesium phosphate separately, ammonium sulfate separately, then all poured together, a substrate added, and the whole admixture allowed to react precipitate together and separate out to form one of my catalysts.

Of course, it is within the concept of my invention to utilize combination solutions, such as a mixture of aluminum sulfate and potassium aluminum sulfate in my first aqueous solution; sodium metasilicate and lithium disilicate in making up my second aqueous solution; ammonium monohydrogen phosphate together with sodium pyrophosphate in making up one of the solutions. Furthermore it would be within the compass of my invention to select suitable salts from each appropriate group, salts in the dry form will not necessarily be anhydrous, together with a substrate, in suitable amounts and proportions according to my invention; physically mix them thoroughly together, preferably in a finely divided form or by grinding; stir the whole mixture into water, allow the precipitation and settling to take place; and then perform the necessary separation and drying steps. Mixed substrates, of course, can be used. Once having the knowledge of the catalysts of my invention, one skilled in the art can readily determine a variety of approaches in preparation of the catalysts.

All of my catalysts, as I have described them, are solid materials after preparation. The particular form of the catalyst as to particle size is not critical, but is chosen according to suitability for a particular catalytic reactor. Normally, the prepared catalysts will be in rather finely divided particulate form. If desired, the catalysts can be formed into pellets or lumps or granules according to requirements for a particular reactor, or the type of catalyst bed to be used, or the zone for contacting the lactam vapor.

Lactam Conversion

The conversion itself, the ammonialytic cleavage, usually is effected in the gaseous phase. The catalysts are solids. The contacting of the gaseous lactam phase with the solid catalysts can be by any conventional method, such as passing a gaseous stream of lactam and ammonia vapors through a fixed bed of catalyst, or through a fluidized bed of catalyst, or otherwise as may be convenient.

Thus it is necessary, first, to produce a vaporous stream of at least one lactam. The ammonia portion of the vapor stream can be added as the lactam is vaporized, or added separately after the lactam is vaporized, or added as a gaseous phase to a liquid lactam-diluent or dispersant solution. For example, the lactam can be melted into a molten or a liquid form and ammonia gas passed therethrough, the effluent vapors or gases then form a stream which is a mixture of ammonia vapor and lactam vapor. The stream is conducted to a contacting or reaction zone wherein the ammonialytic cleavage is promoted by my catalyst. If desired, the ammonia can be heated prior to passing through the molten lactam.

Alternatively, the lactam can be dissolved in a suitable solvent, ammonia gas passed therethrough, and the resulting effluent gaseous stream then contains vaporized lactam plus ammonia vapor plus vaporized solvent. A more usual procedure is to prepare the lactam-diluent solution-dispersion, admix therewith ammonia gas to form a mixed liquid-gas admixture, and conduct this admixture stream to the hot contacting zone containing the catalyst where the liquid is vaporized and ammonialytic cleavage occurs in the vapor state. Vaporization can be effected prior to the contacting zone, if desired.

The reaction temperatures for ammonialytic cleavage can be in the range of about 250° to 750° C.; though more preferably in the range of about 350° to 500° C. Pressures in the range of about 0.1 to as much as 1000 atmospheres can be employed in the reaction zone. More usually, the pressures are within the range of about 1 to 100 atmospheres. Atmospheric pressure is certainly convenient, quite suitable, and therefore frequently employed. The reaction itself can be effected within a range of about 0.1 second to 10 hours, though usually times of between about 1 and 10 seconds are suitable to obtain desired conversion.

While a minimum of 1 mole of ammonia per mole of lactam is required in these reactions, the amount of ammonia actually employed can range up to as much as 1000 moles per mole of lactam. Excess ammonia not consumed in the reaction can ultimately be recovered, such as by condensation, and recycled for reuse. The amount of excess ammonia feasible to employ is limited primarily by economic considerations as to amounts of materials convenient to handle, recover, and recycle. In practice, somewhat more than the minimum amount of ammonia is normally employed, usually at leat 10 moles per mole of lactam, since more effective cleavage is obtained thereby.

Examples of the group of lactams wherein $n$ is in the range of from about 3 to 9 include the following as illustrative examples:

6-Aminohexanoic acid lactam
4-aminobutyric acid lactam
10-aminodecanoic acid lactam
10-amino-3-ethyl-5-octadecanoic acid lactam 4-amino-2-methylbutyric acid lactam
10-amino-3-cyclohexyldecanoic acid lactam
8-amino-4,4-decyclopentaoctanoic acid lactam
10-amino-6-phenyldecanoic acid lactam
10-amino-4-butyl-6-phenyldecanoic acid lactam
6-amino-3-benzylhexanoic acid lactam
5-amino-4-(3-ethylcyclohexyl)pentanoic acid lactam
7-amino-5-(3,5-dimethylphenyl)heptanoic acid lactam
8-amino-3-(4-ethylcyclohexyl)octanoic acid lactam
8-amino-2,2,4,4,6,6-hexamethyloctanoic acid lactam
9-amino-2-ethyl-3-methyl-6-phenylnonanoic acid lactam
5-amino-pentanoic acid lactam and the like.

Diluents can be utilized to make up as much as 90 weight percent of the total mixture comprised of lactam, ammonia and diluent. Suitable diluents include cyclic hydrocarbons, such as aromatics including benzene, toluene, xylene, and the like; as well as the cycloparaffins including cyclopentane, cyclohexane, and the like. Cyclic ethers also are suitable and include tetrahydrofuran, tetrahydropyran, and the like. Specifically, any diluent can be employed which is substantially nonreactive within the reaction environment, and which will effectively dissolve or disperse the lactam to be cleaved. Desirably, diluents are employed which can be subsequently used to azeotrope water from the reaction mixture which will include diluent, unreacted lactam, unused ammonia, the desired ω-aminonitrile, as well as water. Water, of course, is a product of the reaction at the rate of one mole per mole of lactam cleaved.

The ω-aminonitrile produced can be recovered from the reaction mixture by any means known to the art. U.S. Letters Pat. No. 2,900,310, issued to Johannes H. Ottenheyn Aug. 18, 1959, discloses one suitable means of separating the desired ω-aminonitriles.

The foregoing discussion and examples disclose that my complexes of magnesium-aluminum-phosphate-silicate on substrates are highly effective catalysts, particularly to catalyze the ammonialytic cleavage of lactams to the corresponding ω-aminonitriles. Reasonable variations and modifications of the process of my invention and the catalysts of my invention are possible without departing from the scope and spirit of my disclosure as set forth in the specification hereinabove and the claims hereinafter.

I claim:

1. A composition consisting essentially in combined form of magnesium, aluminum, phosphate, and silicate, on a substrate.

2. A catalyst comprising in combined form magnesium, aluminum, phosphate, and silicate, on a substrate, wherein the mole ratio of Mg:Al is about 99:1 to 1:99 and the mole ratio of silicate:phosphate is about 99:1 to 1:99, and wherein the amount of said magnesium, aluminum, phosphate, and silicate together is 0.5 to 99.5 weight percent of said catalyst.

3. A catalyst as defined according to claim 2 wherein said mole ratio is about 5:1 to 1:5; said weight percent is about 15 to 50 weight percent; and wherein said substrate is at least one of silica, alumina, and combination substrates containing at least one thereof.

4. A method of preparing a catalyst which comprises the steps of:
a. bringing together in aqueous dispersion ions of magnesium, aluminum, phosphate, and silicate, in the presence of a substrate,
b. separating insoluble components from said aqueous dispersion,
c. recovering said insoluble components as said catalyst comprising in combined form of magnesium-aluminum-phosphate-silicate on said substrate wherein the mole ratio of magnesium:aluminum is about 99:1 to 1:99 and the mole ratio of silicate:phosphate is about 99:1 to 1:99, and wherein said magnesium-aluminum-phosphate-silicate constitutes about 0.5 to 99.5 weight percent of said catalyst.

5. A method according to claim 4 wherein said mole ratio is about 5:1 to 1:5, and said weight percent is about 15 to 50.

6. A method according to claim 4 wherein salts containing said ions are mixed in essentially dry form with said substrate and form an admixture, and which further is admixed with water thereby forming said aqueous dispersion in said step (a).

7. A method according to claim 5 wherein said step (a) comprises:
preparing a first aqueous dispersion comprising water, a magnesium sulfate, and an aluminum sulfate,
preparing a second aqueous dispersion comprising water, a silicate of an alkali metal or ammonium, and a phosphate of an alkali metal or ammonium,
suspending in at least one of said first aqueous dispersion and said second aqueous dispersion a substrate of an alumina, silica, mixtures thereof, or combination substrates containing at least one thereof,
adding said second aqueous solution to said first aqueous solution to form an admixture including said substrate.

8. A method according to claim 7 wherein said insoluble components from said step (c) are further:
d. washed, and
e. dried.

9. A method according to claim 7 wherein said substrate is at least one of α-alumina, η-alumina γ-alumina, fluoride compound-treated alumina, alumina-boria, alumina-zirconia, alumina-beryllia, silicon dioxide, silica-zirconia, silica-titania, silica-boria, silica alumina, silica-alumina-zirconia, silica-alumina-beryllia, silica-alumina-titania, silica-alumina-boria, or mixtures of at least two thereof.

10. A method according to claim 9 wherein said alkali metal is lithium, sodium, potassium, rubidium, cesium, or mixtures thereof.

11. A process according to claim 10 wherein said aqueous solutions are solutions of magnesium sulfate, aluminum sulfate, sodium silicate, and sodium phosphate, and wherein said support is alumina, silica gel, or diatomaceous earth.

12. The catalyst composition comprising in combined form magnesium, aluminum, phosphate, and silicate, on a substrate, wherein said magnesium and said aluminum each are in a chemically combined form, and wherein said catalyst composition is prepared by the coprecipitation of said magnesium-aluminum-phosphate-silicate on said substrate from aqueous solutions containing water-soluble salts of said magnesium, silicate, aluminum, and phosphate,
wherein in said catalyst composition said magnesium-aluminum-phosphate-silicate represents about 0.5 to 99.5 weight percent relative to said substrate, the mole ratio of magnesium:aluminum about 99:1 to 1:99, and the mole ratio of silicate-phosphate ranges about 99:1 to 1:99, such that a balance of cations:anions is effected in said magnesium-aluminum-phosphate-silicate portion of said catalyst composition.

* * * * *